United States Patent [19]
Wideman, Jr. et al.

[11] Patent Number: 6,127,421
[45] Date of Patent: *Oct. 3, 2000

[54] IN OVO USE OF L-ARGININE AND SALTS THEREOF IN THE PREVENTION AND/OR TREATMENT OF PULMONARY HYPERTENSION SYNDROME IN AVIANS

[75] Inventors: Robert F. Wideman, Jr.; Walter G. Bottje, both of Fayetteville, Ark.

[73] Assignee: The Board of Trustees of the University of Arkansas, Little Rock, Ak.

[ * ] Notice: This patent issued on a continued prosecution application filed under 37 CFR 1.53(d), and is subject to the twenty year patent term provisions of 35 U.S.C. 154(a)(2).

[21] Appl. No.: 08/791,589

[22] Filed: Jan. 31, 1997

Related U.S. Application Data

[60] Provisional application No. 60/010,905, Jan. 31, 1996.

[51] Int. Cl.$^7$ .................................................. A61K 31/19
[52] U.S. Cl. ............................................................. 514/565
[58] Field of Search ............................................... 514/565

[56] References Cited

U.S. PATENT DOCUMENTS

| | | | |
|---|---|---|---|
| 5,158,883 | 10/1992 | Griffith | 435/240.2 |
| 5,213,815 | 5/1993 | O'Brien | 424/935 |
| 5,217,997 | 6/1993 | Levere et al. | 514/565 |

OTHER PUBLICATIONS

Owen, et al. "Effect of Age Exposure and Dietary Acidification or Alkalinization on Broiler Pulmonary Hypertension Syndrome", 1994 J. Appl.Poultry.Res.3:244–252.

Wideman et al. "Preventing Ascites with Pulmonary Vasodilators", Proceedings of the Meeting Arkansas Nutrition Conference, Arkansas Poultry Federation, Sep. 13–15, 1994.

Taylor, et al "Dietary Arginine Influences Rous Sarcoma Growth in a Major Histocompatibility B Complex Progressor Genotype", *Society for Experimental Biology and Medicine*, 1992, pp. 38–41.

Subcommittee on Poultry Nutrition, Committee on Animal Nutrition, Board of Agriculture, "Nutrient Requirements of Poultry", *National Research Council*, 9$^{th}$ Ed., 1994, pp. 27–43.

*Primary Examiner*—Raymond Henley, III
*Attorney, Agent, or Firm*—J. M (Mark) Gilbrath; Robert W. Strozier; Gilbrath & Strozier

[57] ABSTRACT

A method of treating an avian egg, including the step of administering to an avian egg a sufficient amount of an L-arginine compound to prevent pulmonary hypertension syndrome in an avian to be hatched from the egg.

7 Claims, 2 Drawing Sheets

IN OVO USE OF L-ARGININE AND SALTS THEREOF IN THE PREVENTION AND/OR TREATMENT OF PULMONARY HYPERTENSION SYNDROME IN AVIANS

RELATED APPLICATION DATA

This application claims priority from U.S. Provisional application Ser. No. 60/010,905 filed Jan. 31, 1996.

BACKGROUND OF THE INVENTION

1. Field of the Invention

The present invention relates to treatment of avians. In another aspect, the present invention relates to the use of L-arginine for the treatment of avians. In even another aspect, the present invention relates to the administration of L-arginine to avians in ovo for the treatment of or prevention of pulmonary hypertension syndrome, also commonly known as ascites in poultry.

2. Description of the Related Art

Pulmonary hypertension syndrome was reported as early as 1968, and is a condition characterized by mortality with the accumulation of fluid (ascites fluid) in the abdomen of the bird. Ascites fluid accumulation in the body cavity may also be caused by tumor growth in the abdominal cavity. Pulmonary hypertension syndrome is caused by a high resistance to blood flow through the lungs. This excessive resistance of blood flow through the lungs causes an adverse effect on the heart, and hence pulmonary hypertension syndrome. As used hereinafter, "ascites" and "pulmonary hypertension syndrome" will be used interchangeably with the understanding that this form of ascites in poultry is in no way related to tumor growth.

Pulmonary hypertension syndrome poses a serious problem to young fast growing poultry all over the world. First associated with flocks raised at high altitude, it is now recognized that other factors, such as cold temperatures, rapid growth, respiratory distress, high salt intake, and poor ventilation, also encourage pulmonary hypertension syndrome. Death from pulmonary hypertension syndrome results due to an enlarged heart, specifically including dilation and hypertrophy of the right ventricle. Congestive heart failure develops leading to liver damage, and kidney lung and intestinal problems, and compression of the air sac with abdominal fluids. While traditionally, male birds were at greater risk than females because of their faster growth rate, the conditions of modern poultry farming have caused female birds to suffer almost equally.

Pulmonary hypertension syndrome was originally confined to countries such as Bolivia, Columbia, Mexico, Peru, and South Africa, where poultry are traditionally raised at high altitude. It has now been reported in virtually all countries with intensive poultry production practice using modern broiler strains.

The commercial impact of pulmonary hypertension syndrome can be devastating. In fact, mortality among some United States poultry flocks can commonly amount to 5% of birds "started", and in some cases can range to over 30% of birds started. This results in millions of dollars lost due to ascites.

It has been reported that it now appears that there has been a marked increase in the incidence of pulmonary hypertension syndrome in low altitude countries such as the United Kingdom, Italy, Germany, Australia and Mauritius. It has also been reported that recent evidence tends to show that ascites is now increasing during warmer weather and is now appearing at a younger age in poultry.

U.S. Pat. No. 5,217,997, issued Jun. 8, 1993 to Levere et al. discloses the use of L-arginine or a pharmaceutically acceptable salt thereof in the treatment of hypertension, bronchial asthma, and high vascular disorders in mammals. Such high vascular resistance disorders in mammals include primary or secondary vasospasm, angina pectoris, cerebral ischemia and preeclampsia of pregnancy. As disclosed, about 1 mg to about 1500 mg per day of the L-arginine or a pharmaceutically acceptable salt thereof is administered to the mammal.

U.S. Pat. No. 5,158,883, issued Oct. 27, 1992 to Griffith, discloses a method of treating mammal cells using amino arginine to block nitric oxide formation in-vitro. Typical dosages are administered in a nitric oxide synthesis inhibiting amount, generally in the range of about 10 $\mu$g/kg to 100 mg/kg.

U.S. Pat. No. 5,213,815, issued May 25, 1983 to O'Brien, discloses a method of treating and preventing ascites in poultry by administering a combination of Eyebright herb and Brewer's yeast to poultry. Prevention of ascites is accomplished by adding Brewer's yeast to poultry food at a rate of about 40 grams per 160 pounds of poultry, starting from "day old" and continuing through the last day of "grow out". Treatment of ascites is accomplished by supplementing the Brewer's yeast with Eyebright herb at a rate of 500 mg per 160 pounds poultry per day for seven days.

"Dietary Arginine Influences Rous Sarcoma Growth in a Major Histocompatibility B Complex Progressor Genotype", Taylor et al., Society for Experimental Biology and Medicine, 1992, at 38–41, discloses administering five week-old chickens feed having either 0.92% or 2.40% L-arginine content to lower tumor growth. While the article reports lower tumor growth from feed high in L-arginine, it discloses that mortality was not significantly different between a low and high L-arginine diet. Additionally, this article is silent regarding treatment of chickens having pulmonary hypertension syndrome, is silent regarding administration of L-arginine prior to five weeks after hatching.

The "Nutrient Requirements of Poultry", by the Subcommittee on Poultry Nutrition, Committee on Animal Nutrition, Board of Agriculture, National Research Council, 9th Ed., 1994, at 27–42, recommends providing broilers with feed having 1 to 1.25 wt% arginine, turkeys with feed having 0.5 to 1.6 wt% arginine, and ducks feed having from 1 to 1.1 wt% arginine.

However, in spite of these advancements in the prior art, none of these prior art references disclose or suggest the administration of L-arginine to avians for the treatment and/or prevention of pulmonary hypertension syndrome.

Thus, there is still a need for a method of treating and/or preventing pulmonary hypertension syndrome in avians.

These and other needs in the art will become apparent to those of skill in the art upon review of this specification, including its drawings and claims.

SUMMARY OF THE INVENTION

It is an object of the present invention to provide for a method of treating avians.

It is another object of the present invention to provide for a method of administering L-arginine to avians.

It is even another object of the present invention to provide for a method of administering L-arginine to avians to treat and/or prevent pulmonary hypertension syndrome.

It is still another object of the present invention to provide for a method of administering L-arginine to avians in ovo to treat and/or prevent pulmonary hypertension syndrome.

These and other objects of the present invention will become apparent to those of skill in the art upon review of this specification, including its drawings and claims.

According to one embodiment of the present invention there is provided a method of treating an avian egg. The method generally includes administering to an avian egg a sufficient amount of an L-arginine compound to prevent pulmonary hypertension syndrome in an avian to be hatched from the egg. In more specific embodiments, the L-arginine compound may be injected into the egg or diffused into the egg.

In the embodiment above, the L-arginine compound comprises at least one selected from the group consisting of L-arginine, substituted L-arginine, L-arginine salts, organo L-arginines, and compounds comprising a form or derivative of L-arginine.

DETAILED DESCRIPTION OF THE INVENTION

Figure 1:
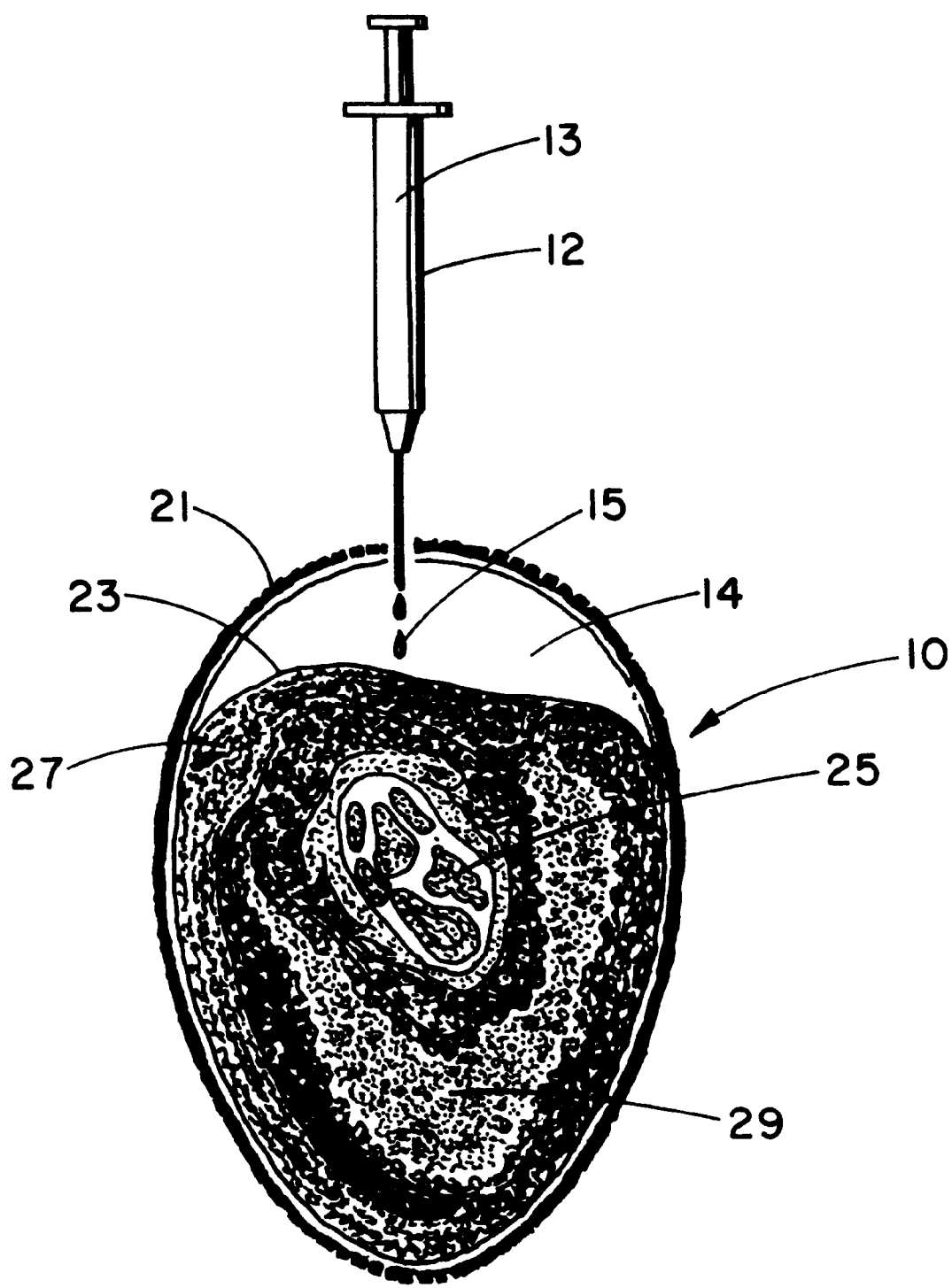
FIG. 1 is a cross-sectional view of an avian egg, showing the in ovo injection of L-arginine through the egg shell and into the air chamber.

One embodiment of the method of the present invention generally includes the administration of an L-arginine compound to avians.

Another embodiment of the method of the present invention generally includes the administration of an L-arginine compound to an avian embryo in ovo.

The L-arginine compound may be administered to an avian by any route of administration. Suitable routes of administering the L-arginine compound to an avian would, of course, include oral, parenteral, topical, injection, aerosols, sprays, mists, and the like. Preferably, in the practice of the method of the present invention, the L-arginine compound is orally administered to an avian, most preferably in conjunction with the feed.

The amount of L-arginine compound to be utilized in the practice of the present invention, will be that amount suitable to treat and/or prevent pulmonary hypertension syndrome. Generally, the amount of L-arginine compound to be utilized in the practice of the present invention, will depend upon the size and type of avian, the specific form of the arginine compound utilized, the method of administration, pen conditions, as well as other factors.

Generally, when incorporated into feed, the L-arginine compound will generally comprise in the range of at least about 1.5 weight percent of the feed. Preferably, the L-arginine compound will comprise at least about 1.8 weight percent of the feed. More preferably, the L-arginine compound will comprise at least about 2.0 weight percent of the feed, even more preferably greater than about 2.4 weight percent of the feed, and most preferably at least about 2.6 weight percent of the feed. The upper level for the amount of L-arginine compound to be utilized will generally be controlled by economic factors, by any undue effects caused by L-arginine (at present inventors know of none), toxicity levels, and by other physical limitations. The upper level for the amount of L-arginine in the feed is preferably about 10 weight percent of the feed, more preferably about 8 weight percent of the feed, even more preferably about 5 weight percent of the feed, and most preferably about 3 weight percent of the feed.

When incorporated into the feed, it is to be understood that the L-arginine compound may be added to the feed at any time during the pelletizing process. Alternatively, the L-arginine compound may be applied to the surface of the feed either in dry form or as part of a solution, suspension or emulsion that dries and leaves residual L-arginine.

In the practice of the present invention, diffusion of the L-arginine compound through the shell of and into the egg may be achieved by contacting at least a portion of the egg with a liquid or gel comprising the L-arginine compound. For this diffusion embodiment, the L-arginine compound may be solubilized into the liquid or gel, may exist as a paste with the liquid or gel, may exist as suspended particles in the liquid or gel, or may be emulsified with the liquid or gel. Non-limiting examples of suitable liquids or gels useful as carriers for diffusing the L-arginine compound into the egg include water, DMSO, buffered saline solutions, physiological saline solutions, deionized water, glycerol gels, and oil based and fat based carriers.

For the diffusion process, the contacting of at least a portion of the egg with a liquid or gel comprising the L-arginine compound may be accomplished by submerging at least a portion of the egg into the liquid or gel, or by applying the liquid or gel to the surface of the egg. The liquid or gel may be applied to the surface of the egg by any suitable method, including spraying, pouring, dripping, wiping, coating, brushing, blotting, and the like.

Diffusion of the L-arginine compound through the egg shell and into the egg is accomplished more quickly by utilizing high concentrations of L-arginine compound containing solution, gel, emulsion or suspension. Generally, for suitable diffusion into the egg, the L-arginine compound containing solution, gel, emulsion or suspension, will comprise at least about 0.01 wt %, preferably at least about 1 wt %, more preferably at least about 5 wt %, even more preferably at least about 10 wt %, and most preferably at least about 20 wt % L-arginine compound. The upper level for the amount of L-arginine compound to be utilized will generally be controlled by economic factors, by any undue effects cause by L-arginine (at present inventors know of none), toxicity levels, and by other physical limitations.

When administering the L-arginine to an embryo, it is preferable to inject the L-arginine compound directed into the egg, preferably the air chamber. For example, this can be accomplished by utilizing about a 24 or 26 gauge needle, or for large scale injection of a flock commercial injection machines are available.

The amount of L-arginine compound injected or diffused into the egg will be that amount sufficient to adequately treat and/or prevent pulmonary hypertension syndrome. Generally at least about 0.1 mg is injected or diffused into the egg, preferably at least about 1 mg, more preferably at least about 10 mg, and most preferably at least about 20 mg.

The upper level for the amount of L-arginine compound to be injected or diffused into the egg will generally be controlled by economic factors, by any undue effects cause by L-arginine (at present inventors know of none), toxicity levels, and by other physical limitations.

Referring now to FIG. 1, there is shown one embodiment of method of the present invention for administering an L-arginine compound to the avian embryo in ovo. Egg 10 includes egg shell 21, air chamber 14, chorloallantoic membrane 23, albumen 27, yolk 29, and embryo 25. A an injector 12, which in the embodiment shown is a syringe, contains L-arginine compound 13 and is utilized to provide L-arginine compound 15 to air chamber 14 where it will be absorbed into the embryo 25.

While the inventors believe that the L-arginine compound may be injected into the egg at any time prior to hatching, it is convenient to inject the eggs in conjunction with vaccination. Generally in many commercial operations, at about the 15 to 18 day point the eggs are candled and vaccinated. Since the eggs are already being handled during the candling and vaccination process, it is convenient to inject the L-arginine compound at this time. In fact, if the L-arginine is compatible with the vaccine, they may be injected together.

L-arginine compounds suitable for use in the practice of the present invention any form of L-arginine, any substituted L-arginine, and any compound incorporating a form of L-arginine, provided that the desired effect of treating ascites is obtained. Examples of suitable L-arginine compounds include L-arginine (free base), substituted L-arginines, organo L-arginines, L-arginine salts, and any other suitable form of L-arginine. Preferably, the L-arginine compound comprises L-arginine in a free base form.

Suitable anions for salts of L-arginine which may be utilized include bromide, fluoride, iodide, borate, hypobromite, hypochlorite, nitrite, nitrate, hyponitrite, sulfate, disulfate, sulfite, sulfonate, phosphate, diphosphate, phosphite, phosphonate, diphosphonate, perchlorate, perchlorite, oxalate, malonate, succinate, lactate, carbonate, bicarbonate, acetate, benzoate, citrate, tosylate, permanganate, manganate, propanolate, propanoate, ethandioate, butanoate, propoxide, chromate, dichromate, selenate, orthosilicate, metasilicate, pertechnetate, technetate, dimethanolate, dimethoxide, thiocyanate, cyanate, isocyanate, and the like. The suitable cation for most salts is hydrogen, however, other cations such as sodium, potassium and the like would be acceptable in the preparation of such a salt. It would advantageous if the specific salt form selected allowed a pH close to neutral.

The inventors believe that the L-arginine compound is most effective at preventing pulmonary hypertension syndrome if it is administered from the embryonic stage until slaughter. Obviously, economic factors may dictate a much more limited use of the L-arginine compound. If the L-arginine compound is not administered to the embryo, it is preferred that commencement of administration of the L-arginine compound begin soon after hatching, preferably before the avians are five weeks old, and most preferably before the avians are three weeks old.

As an alternative, pen conditions could be monitored, and at the onset of conditions likely to encourage pulmonary hypertension syndrome, or once it is recognized that birds in the flock are suffering from hypertension syndrome, L-arginine compound could be administered to the flock. For example, once temperatures drop below the avian's thermoneutral zone, about 85° F. for hatching chicks, about 70° F. for 5 week old chicks, and about 68° F. for 6 week old chicks, the incidence of pulmonary hypertension syndrome will increase. As another example, once temperatures drop, the chicken houses are closed up and heated, with ventilation of fresh air reduced to preserve heat. Conditions of poor ventilation result in increased rates of pulmonary hypertension syndrome. Exposure to agents of respiratory distress, i.e. certain bacteria, dusts, ammonia and viruses, are also known to cause pulmonary hypertension syndrome. Finally, in some instances, feed is obtained which is high in salt, i.e., bakery products such as pretzel flour. High salt diets are also linked to an increase in pulmonary hypertension syndrome.

The present invention is believed to be suitable for treating any avian suffering from pulmonary hypertension syndrome. Generally, such avians which may be treated by the present invention includes chicken, turkey, duck, pheasant, quail, geese, ostrich and emu. Preferably, the present invention is utilized in the treatment of chicken, turkey and duck. Most preferably, the present invention is utilized in the treatment of chicken.

EXAMPLES

The following examples are provided merely to illustrate the present invention, and are not intended to limit the scope of the claims.

Example 1

At 1 d, 650 male by-product chicks of the Hubbard Breeder Pullet (Hubbard Farms, Walpole, N.H. 03608) line were wing banded, weighed, and randomly distributed in 24 floor pens (52.5 $ft^2$ per pen) on built-up rice hull litter. The chicks were brooded at 32, 29, and 27 C. during Weeks 1, 2, and 3, respectively. They were weighed and culled at 21 d of age, leaving 25 chicks in each of 24 pens. This example was conducted from October through December of the year, when outside temperatures averaged 20 C. or lower. Beginning on Day 21 and continuing until the termination on Day 54, thermostatically regulated brooders and ventilation fans were adjusted daily to maintain an average house temperature of 10 to 15 C., thereby triggering a sufficient incidence of Pulmonary Hypertension Syndrome ("PHS") to permit statistical evaluation of the protective efficacy of supplemental dietary L-arginine Hcl. All chicks were fed the same commercial corn-soybean meal-based broiler starter ration (CP, 21.59%; ME, 3,126 kcal/kg; lysine, 1.174%; arginine, 1.589%) for the first 20 d. On Day 21 the pens were randomly assigned to one of four diet treatment groups, with six pen replicates per diet treatment. The CONTROL birds were fed a pelleted corn-soybean meal-based grower ration (CP, 19.07%; ME, 3,213 kcal/kg; lysine, 0.991%; arginine, 1.387%). Birds in the remaining groups were fed the grower ration to which L-argine HCl (L-ARG: anhydrous L-arginine monohydrochloride, available from Ajinomoto Co. Inc., Tokyo, Japan) had been added at levels of 0.25, 0.5, or 1% by weight prior to pelleting. During the Day 41 to 54 finisher period, all birds were fed a commercial corn-soybean mash-type finisher ration without any added arginine (CP, 17.71%; ME, 3,253 kcal/kg; lysine, 0.891%; arginine, 1.278%). The starter, grower and finisher rations were formulated to meet all other minimum NRC (1984) recommendations. Feed consumption per pen was recorded for Days 1 to 20, 21 to 40, and 41 to 54, and body weights were recorded on Days 1, 21, and 54.

Example 2

Male by-product chicks of the Hubbard Breeder Pullet line were fed the same starter ration and brooded as described above until Day 21, when they were randomly distributed among 24 pens with 25 chicks per pen. This Example 2 was conducted from January through March of 1994. Beginning on Day 21 and continuing until Day 56, the average house temperature was maintained between 10 and 15 C. Birds in 12 pens were fed the unsupplemented grower and finisher rations as described for Example 1 above (CONTROL group), birds in 6 pens were fed the grower ration supplemented with 1% L-arginine HCl (Days 21 to 42: L-ARG/CONTROL group), and birds in the remaining 6 pens were fed the grower and finisher rations supplemented with 1% L-arginine HCl (Days 21 to 56: LARG/L-ARG group). Feed consumption per pen was recorded for Days 1 to 21, 22 to 42, and 42 to 56, and body weights were recorded on Days 1, 21, and 56. The three largest clinically healthy birds were selected from each pen on Day 55. Standard electrocardiograms were recorded to evaluate lead-II R-S wave amplitude as an index of cardiac hypertrophy. Blood samples were obtained for micro-hematocrit determinations and, after killing the birds by cervical dislocation, the heart was removed, blotted dry, and dissected to calculate ventricular weight ratios as an index of pulmonary hypertension.

In both experiments, feed and water were provided for ad libitum consumption. Temperature extremes were recorded daily with High-Low thermometers placed at bird level in four widely separate locations. Necropsies were performed to identify all PHS-related mortality occurring after Day 21. Birds were included in the total PHS mortality if they died with ascites, or if they died with obvious pre-PHS symptoms including right ventricular dilation, hydropericardium, and vascular congestion.

Statistical Analysis For Examples 1 And 2

Feed conversion ratios were calculated by dividing the cumulative feed consumption per pen by the live body mass per pen at the end of each measurement period, without adjusting for the body mass of birds that died. Daily and cumulative PHS mortality were tabulated as the percentage of birds in each pen dying from PHS. Data were analyzed using the General Linear Models procedure of SAS (SAS Institute, 1982) with means separated using Turkey HSD or orthogonal contrasts.

Discussion of Examples 1 and 2

House temperatures recorded during Examples 1 and 2 averaged below 15 C., with some unavoidable variability due to fluctuating outside temperatures. Samples of the 1% L-ARG grower ration from Example 2 were assayed by Novus International, Inc. (St. Charles, Mo. 63304). The 1% L-ARG ration contained 0.77% supplemental arginine, which is reasonably close to the 0.82% arginine expected on a molar basis to be obtained by adding 1% arginine monohydrochloride to the basal ration.

Figure 2:
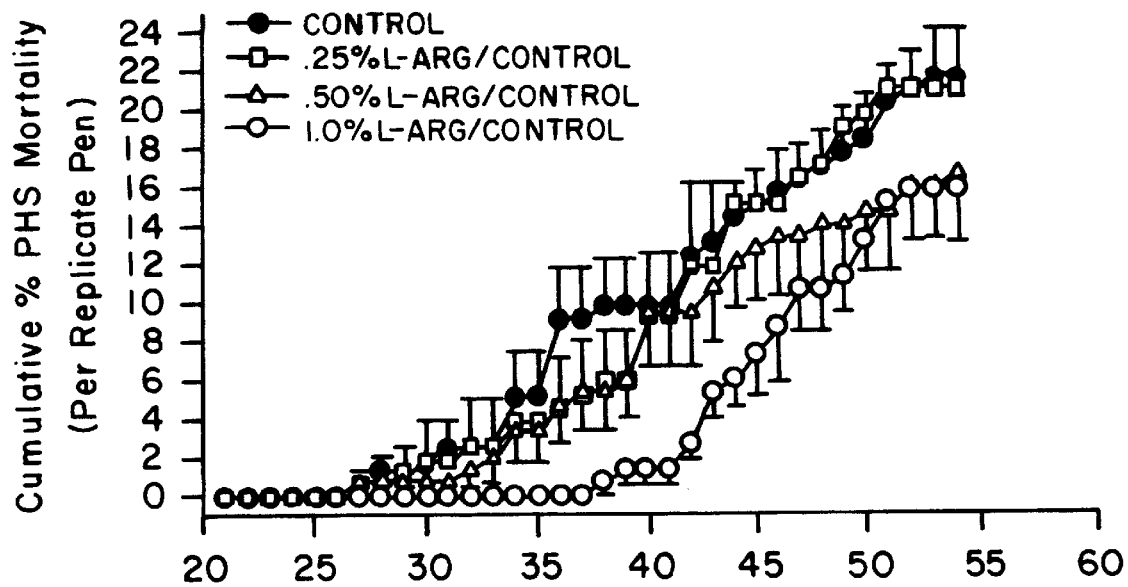
FIG. 2 is a plot of cumulative % pulmonary syndrome mortality on a pen replicate basis (mean ± S.E.M.) for Example 1.
Figure 3:
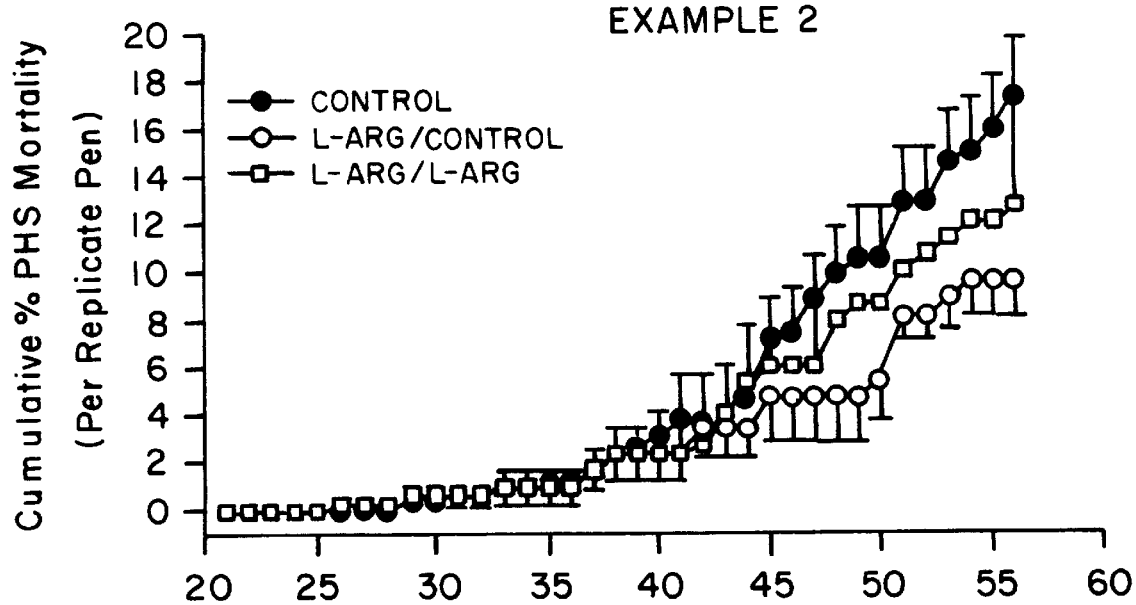
FIG. 3 is a plot of cumulative % pulmonary syndrome mortality on a pen replicate basis (mean ± S.E.M.) for Example 1.

Cumulative percentage PHS mortalities calculated on a pen basis and pooled by treatment are shown for both experiments in FIGS. 2 and 3. The initial mortality due to PHS was recorded 6 to 7 d after exposing the chicks to cool temperatures, and PHS mortality reached 22% (Example 1) and 17% (Example 2) cumulative totals in the Control groups by 54 to 56 d of age. When compared on a daily basis with the CONTROL group in Example 1, cumulative percentage PHS mortality was significantly lower in the 0.25% and 0.5% L-ARG groups on Day 36 (p=0.044 and 0.049, respectively), and in the 1% L-ARG group on Days 34 to 46 (p=0.011). In Example 2, neither the L-ARG/CONTROL nor L-ARG/L-ARG groups had significantly different percentage cumulative PHS mortalities when compared on a daily basis with each other or with the CONTROL group. However, when data from all L-ARG/CONTROL and L-ARG/L-ARG pens were pooled, groups fed diets supplemented with arginine had marginally lower (p=0.065) cumulative PHS mortality for the entire Day 21 to 56 interval when compared with the CONTROL group. In Example 1, mortality not attributed to PHS for the 21 to 54 d period was: 2/125 (CONTROL); 3/125 (0.25% L-ARG); 2/125 (0.5% L-ARG); and, 5/125 (1% L-ARG). In Example 2, non-PHS mortality for the 21 to 56 d period was: 10/300 (CONTROL); 4/150 (L-ARG/CONTROL); and, 5/150 (L-ARG/L-ARG). The non-PHS mortality was not further categorized or quantified.

None of the L-ARG diets significantly affected final body weights or net weight gain when compared with the CONTROL group in either example (Tables 1 and 2). Feed conversion ratios were not consistently altered by supplementing grower or finisher rations with 1% L-arginine HCl in Example 1 (data not shown), although in Example 2 Day 21 to 56 feed conversion ratios were lower for the pooled L-ARG groups when compared with the CONTROL group (Table 3). Feed conversion ratios were high in these experiments, presumably due to the relative inefficiency of by-product-type birds, and due to the anticipated influence of cool temperatures on feed conversion. Body weights on Days 1 and 21, and net weight gain for Days 1–21 did not serve as predictive indices of susceptibility to PHS during the grower and finisher periods (Days 21 to 56) in Example 1 (Table 4) or Example 2 (data not shown). For large healthy birds at the end of Example 2, heart rates and electrocardiogram lead-II R-S wave amplitudes were not significantly affected by L-arginine HCl supplementation (data not shown), nor were hematocrits significantly altered (Table 5). Birds fed diets supplemented with L-arginine HCl (Pooled L-ARG) did have significantly lower right: total ventricular weight ratios than CONTROL birds (Table 5).

TABLE 1

Body weights and net weight gain for birds in experiment 1 fed a grower ration alone (CONTROL) or supplemented with L-Arginine (L-ARG)[1]

| Treatment group | Body Weight | | | Net weight gain | | |
|---|---|---|---|---|---|---|
| | Day 1 | Day 21 | Day 54 | Day 1 to 21 | Day 21 to 54 | Day 1 to 54 |
| | (grams) | | | | | |
| CONTROL | 37.9 ± .7 | 667 ± 26 | 3071 ± 39[ab] | 629 ± 26 | 2404 ± 43 | 3033 ± 39[ab] |
| .25% L-ARG | 37.7 ± .4 | 662 ± 16 | 3030 ± 28[b] | 624 ± 16 | 2368 ± 27 | 2993 ± 28[b] |
| .50% L-ARG | 32.2 ± .6 | 679 ± 18 | 3149 ± 18[a] | 647 ± 20 | 2469 ± 19 | 3116 ± 21[a] |
| 1.0% L-ARG | 38.7 ± .5 | 662 ± 14 | 3042 ± 22[b] | 624 ± 14 | 2379 ± 23 | 3004 ± 22[b] |

[1]Data are Means ± S.E.M. of six pen replicates per treatment.
[a,b]Means within a parameter with no common superscripts differ significantly (p ≤ .05).

TABLE 2

Body weights and net weight gain for birds in experiment 2 fed grower and finisher rations alone (CONTROL) or supplemented with 1% L-arginine during the grower (L-ARG/CONTROL) or grower and finisher (L-ARG/L-ARG) phases[1]

| Treatment group | Body weight | | | Net weight gain | | |
|---|---|---|---|---|---|---|
| | Day 1 | Day 21 | Day 56 | Day 1 to 21 | Day 21 to 56 | Day 1 to 56 |
| | (grams) | | | | | |
| CONTROL | 46.6 ± .8 | 642 ± 6 | 3337 ± 32 | 596 ± 6 | 2695 ± 30 | 3290 ± 31 |
| LARG/CONTROL | 47.3 ± .5 | 631 ± 9 | 3263 ± 21 | 583 ± 9 | 2633 ± 20 | 3216 ± 21 |
| L-ARG/L-ARG | 46.6 ± 1.1 | 635 ± 9 | 3352 ± 17 | 589 ± 10 | 2716 ± 18 | 3305 ± 17 |

[1]Data are Means ± S.E.M. of 12 (control) or 6 (L-arg/control, L-arg/L-arg) pen replicates per treatment.

TABLE 3

Feed Conversion Ratios[1] for birds in experiment 2 fed grower or finisher rations alone (CONTROL) or supplemented with 1% L-arginine during the grower (L-ARG/CONTROL) or grower and finisher (L-ARG/L-ARG) phases[2]

| Treatment Group | Feed conversion ratio | | |
|---|---|---|---|
| | Day 1 to 21 | Day 21 to 56 | Day 1 to 56 |
| | kg feed consumed:kg weight gained | | |
| CONTROL | 1.59 ± .03 | 2.67 ± .07 | 2.39 ± .07 |
| L-ARG/CONTROL | 1.59 ± .04 | 2.46 ± .06[a] | 2.27 ± .05 |
| L-ARG/L-ARG | 1.60 ± .03 | 2.50 ± .14[a] | 2.30 ± .09 |

[1]kg Feed Consumed/kg Weight Gained.
[2]Data are Means ± S.E.M. of 12 (CONTROL) or 6 (L-ARG/CONTROL, L-ARG/L-ARG) pen replicates per treatment.
[a]Pooled L-ARG values compared with Control, p = .052.

TABLE 4

Body weights on days 1 and 21, and net weight gain from day 1–21, for all birds in experiment 1 that subsequently died from pulmonary hypertension syndrome (PHS) or did not develop PHS (NORMAL) during the grower and finisher periods (days 21–54)[1]

| Treatment Group | Category | Day 1 body wt | Day 21 body wt | Days 1 to 21 net gain |
|---|---|---|---|---|
| | | | | (grams) |
| CONTROL | PHS | 38.0 ± 0.8 | 659 ± 15 | 621 ± 15 |
| | NORMAL | 39.5 ± 0.4 | 701 ± 9 | 662 ± 9 |
| .25% L-ARG | PHS | 40.1 ± 1.0 | 691 ± 18 | 651 ± 17 |
| | NORMAL | 38.8 ± 0.5 | 708 ± 9 | 669 ± 9 |
| .50% L-ARG | PHS | 39.8 ± 0.8 | 706 ± 12 | 666 ± 12 |
| | NORMAL | 39.7 ± 0.6 | 710 ± 5 | 670 ± 5 |
| 1.00% L-ARG | PHS | 38.7 ± 0.6 | 678 ± 18 | 639 ± 18 |
| | NORMAL | 39.8 ± 0.7 | 707 ± 5 | 668 ± 6 |

[1]Data are Means ± S.E.M. of six pen replicates per treatment.

TABLE 5

Pulmonary hypertension indices for the three largest and clinically healthiest birds per pen on day 55 of experiment 2[1]

| Parameter | CONTROL (n = 36) | L-ARG/CONT (n = 18) | L-ARG/L-ARG (n = 18) | Pooled L-ARG (n = 36) |
|---|---|---|---|---|
| Hematocrit (%) | 36.6 ± .6 | 35.6 ± .9 | 36.4 ± .6 | 36.0 ± .5 |
| Right Ventricle (g) | 2.87 ± .11 | 2.84 ± .19 | 2.52 ± .12 | 2.68 ± .11 |
| Left Ventricle plus Septum (g) | 8.78 ± .19 | 9.21 ± .25 | 9.42 ± .22 | 9.32 ± .16[a] |
| Right Ventricle Total Ventricle | .25 ± .01 | .23 ± .01 | 21 ± .01 | .22 ± .01[b] |

[1]Data are Means ± S.E.M.
[a]Compared with Control, p = .036.
[b]Compared with Control, p = .022.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

I claim:

1. A method of treating an avian egg, comprising administering to an avian egg a sufficient amount of an L-arginine compound to prevent pulmonary hypertension syndrome in an avian to be hatched from the egg.

2. The method of claim 1 wherein the L-arginine compound is injected into the egg.

3. The method of claim 2 wherein the L-arginine compound comprises at least one selected from the group consisting of L-arginine, substituted L-arginine, L-arginine salts, organo L-arginines, and compounds comprising a form or derivative of L-arginine.

4. The method of claim 3 wherein anions for salts of L-arginine are selected from the group of anions consisting of bromide, fluoride, iodide, borate, hypobromite, hypochlorite, nitrite, nitrate, hyponitrite, sulfate, disulfate, sulfite, sulfonate, phosphate, diphosphate, phosphite, phosphonate, diphosphonate, perchlorate, perchlorite, oxalate, malonate, succinate, lactate, carbonate, bicarbonate, acetate, benzoate, citrate, tosylate, permanganate, manganate, propanolate, propanoate, ethandioate, butanoate, propoxide, chromate, dichromate, selenate, orthosilicate, metasilicate, pertechnetate, technetate, dimethanolate, dimethoxide, thiocyanate, cyanate, isocyanate, and wherein cations for salts of L-arginine are selected from the group of cations consisting of hydrogen, sodium and potassium.

5. The method of claim 4 wherein the L-arginine compound is L-arginine free base.

6. The method of claim 2 wherein the amount of L-arginine compound administered is at least about 0.1 mg.

7. The method of claim 6 wherein the amount of L-arginine compound administered is at least about 1 mg.

* * * * *